United States Patent [19]

Davidson et al.

[11] Patent Number: 4,609,665

[45] Date of Patent: * Sep. 2, 1986

[54] USE OF SELECTED PYRIDINE-N-OXIDE DISULFIDE COMPOUNDS TO TREAT OR PREVENT SWINE EXUDATIVE EPIDERMITIS

[75] Inventors: Jeffrey Davidson, Tulare, Calif.; John G. Babish, Ithaca, N.Y.; John H. Wedig, Guilford, Conn.

[73] Assignee: Olin Corporation, Cheshire, Conn.

[ * ] Notice: The portion of the term of this patent subsequent to Aug. 16, 2000 has been disclaimed.

[21] Appl. No.: 638,924

[22] Filed: Aug. 8, 1984

[51] Int. Cl.4 .............................................. A61K 31/44
[52] U.S. Cl. .................................................... 514/335
[58] Field of Search ........................................ 514/335

[56] References Cited

U.S. PATENT DOCUMENTS

| | | | |
|---|---|---|---|
| 3,818,018 | 6/1974 | Weisse et al. | 260/294.8 J |
| 3,890,434 | 6/1975 | Weisse et al. | 424/70 |
| 4,399,130 | 8/1983 | Davidson et al. | 424/245 |

Primary Examiner—Frederick E. Waddell
Attorney, Agent, or Firm—William A. Simons; Thomas P. O'Day

[57] ABSTRACT

Described is a method for treating an animal for swine exudative epidermitis wherein said animal is administered an effective amount of at least one selected pyridine-N-oxide disulfide compound.

5 Claims, No Drawings

USE OF SELECTED PYRIDINE-N-OXIDE DISULFIDE COMPOUNDS TO TREAT OR PREVENT SWINE EXUDATIVE EPIDERMITIS

BACKGROUND OF THE INVENTION

1. Field of the Invention

This invention relates to the use of selected pyridine-N-oxide disulfide compounds to prevent or treat swine exudative epidermitis.

2. Description of the Prior Art

Swine exudative epidermitis (also known as Greasy Pig Disease) is a skin disease of pigs distinghished by the appearance of acute, generalized seborrhoeic dermatitis. The disease generally affects piglets under about 6 weeks of age, but occasionally groups of pigs up to about 3 months of age suffer from the disease. Many of the affected piglets die from the disease.

It is not certain exactly what bacteria cuases the disease; but Staphylococcus hyicus is strongly suspected. The disease is particularly troublesome and of considerable economic importance because, once developed within a litter, often all piglets will be affected. Such affected piglets may have a diminished appetite. Progressive weakness in the piglets, followed by death in a few days, is the likely occurrence. See D. C. Blood and J. A. Henderson, *Veterinary Medicine* (Third Edition) Bailliere, Tindall & Cassell, London, pages 894 and 895.

Swine exudative epidermitis has in the past been treated by administering antiinfective agents such as antibiotics. However, it has been recently found to be very desirable to replace antibiotics by non-antibiotic drugs. For example, antibiotics effective in human medicine should not be utilized in veterinary medicine in order not to build up a strain resistance against bacteria appearing in human diseases. It is thus very important to find a method for the treatment of swine exudative epidermitis utilizing an active non-antibiotic chemical compound which substantially would overcome the drawbacks of antibiotics utilized so far. U.S. Pat. No. 4,399,136, which issued to Davidson et al on Aug. 16, 1983, claims a method for treating an animal for swine exudative epidermitis wherein said animal is administered at least one metallic salt of pyridine-2-thione-N-oxide. This patent is incorporated herein by reference in its entirety.

BRIEF SUMMARY OF THE INVENTION

The present invention, therefore, is directed to treating an animal for swine exudative epidermitis which comprises administering to said animal an effective amount of at least one pyridine-N-oxide disulfide compound to treat or prevent swine exudative epidermitis; said pyridine-N-oxide disulfide compound selected from (a) 2,2'-dithiobis-pyridine-1,1'-dioxide and (b) adducts of 2,2'-dithiobis-pyridine-1,1'-dioxide, the adducts having the formula

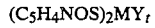

$(C_5H_4NOS)_2MY_t$ wherein M is an alkaline earth metal selected from the group consisting of calcium, magnesium, barium and strontium, Y is an anion selected from the group consisting of halides, sulfates, nitrates, chlorates and acetates, and t is either 1 or 2.

DETAILED DESCRIPTION

The above-noted pyridine-N-oxide disulfide compounds are well known chemicals which may be made by oxidation of the sodium salt of pyridine-2-thione-N-oxide, preferably with hydrogen peroxide or another oxidizing agent. U.S. Pat. No. 2,742,476, which issued to Bernstein et al on Apr. 17, 1956, discloses 2,2'-dithiobis-pyridine-1,1-dioxide and its preparation. The adducts of 2,2'-dithiobis-pyridine-1,1'-dioxide listed in (b) above and their preparation are described in U.S. Pat. Nos. 3,818,018 and 3,890,434, which issued to Weisse et al on June 18, 1984 and June 17, 1975 respectively. All of these U.S. Patents are incorporated herein by reference in their entireties.

Also included in the adducts are hydrates of the aforementioned compounds of formula (I), i.e. adducts including $nH_2O$ groups where n is an integer of 0 to 10.

The preferred compounds for use in this invention are 2,2'dithiobis-pyridine-1,1'-dioxide and the magnesium sulfate trihydrate adduct of 2,2'-dithiobis-pyridine-1,1'-dioxide (i.e. M is magnesium, Y is sulfate and t is 1).

In practicing the process of the present invention, animals such as pigs under the age of about 3 months may be treated with an effective swine exudative epidermitis treating amount of at least one selected pyridine-N-oxide disulfide compound. It is to be understood that the term an effective amount to in the specification and claims herein is intended to include any amount or concentration that will treat or prevent swine epidermitis in such animals. Of course, this amount may be changed in response to numerous variables, such as the degree of effectiveness required, type of metal salt, whether animal is affected by the disease or not, and type of carrier, if any.

For most uses, an effective amount to treat or prevent swine exudative epidermitis would advantageously include administerinq from 1 to about 5 doses comprising from about 15 to about 200 milliliters of an aqueous suspension or dispersion containing about 1.5% to about 5.0% of said active compound or active compounds (from about 225 mg to about 10,000 mg) in intervals from about 12 to about 48 hours. Preferably, said doses comprise from about 20 to about 50 milliliters of an aqueous suspension or dispersion containing about 2% to about 2.5% by weight of active compound per dose (from about 400 mg to about 1250 mg) and said doses are administered about each 12 to 24 hours. Furthermore, the active compound used in the present process may be combined with other known veterinary and pharmaceutical agents for further benefits.

This step of administering these selected pyridine-N-oxide disulfide compounds to the animal is preferably accomplished in the form of a liquid suspension; i.e., the composition is sprayed onto the skin of the pig. Such compositions would comprise the active compound or compounds and at least one vehicle or carrier suitable for administration onto the skin of the animal.

Another preferred way of administering the active compound is by applying it in a cream or the like wherein the skin is covered with an effective amount of the active compound to treat or prevent swine exudative epidermitis.

Sometimes a piglet or mother pig (sow) should be treated, as a preventive measure, even if it is not clear whether the pig suffers from swine exudative epidermitis. For instance, in case it is clear that some animals of a piglet litter are suffering from swine exudative spidermitis, then one may want to treat all animals of said litter in order to assure that no further animals would be infected. Thus, prevention as well as treatment of this disease is contemplated within the scope of the invention.

If one or more active compounds of the present invention is combined with a solid or liquid vehicle or carrier before application, then any suitable methods for formulating and applying the active compound or compounds may be employed. Included in such suitable methods of application are emulsifiable liquids, suspensions, creams, and ointments.

Emulsifiable liquids may be prepared by dispersing the active compound or compounds in a vegetable oil or mineral oil, such as peanut oil, corn oil, soybean oil, sesame oil, and the like, and then admixing the thus formed suspensions with a suitable surfactant or emulsifier.

Suspensions are generally formed by dispersing the active compound or compounds in water or a suitable aqueous solution or other solvent.

Creams and ointments are generally made the same as emulsified liquids except at least one gelling agent or the like is additionally added. Such gelling agents may be natural waxes like beeswax or aluminum fatty acid salts (e.g., stearates, palmitates, and oleates).

It should be clearly understood that any of the above-noted formulations, the ingredients which may make up such formulations other than the active compound or compounds and their dosage, and means for applying these formulations may include all known and conventional substances, amounts, and means, respectively, that are suitable for obtaining the desired swine exudative epidermitis treatment or prevention result. Therefore, such process parameters are not critical to the present invention.

Besides the above-noted active compounds the present invention also contemplates the use of similar pyridine-2-thione-N-oxide compounds to treat swine exudative epidermitis. Specifically, the present invention contemplates the use of free 2-mercaptopyridine-N-oxide, organic salts (e.g., t-butylamine) and adducts of 2-mercaptopyridine-N-oxide. The present invention also contemplates the use of similar compounds which have one or more other substituents on the pyridine ring (e.g., lower alkyl groups, $NO_2$, or halogens).

The following Examples further illustrate the present invention. All parts and percentages are by weight unless explicitly stated otherwise.

EXAMPLE 1

Minimum Lethal Concentration (MLC) Values of Magnesium Sulfate Trihydrate Adduct of 2,2'-Dithiobis-Pyridine-1,1'-Dioxide A freeze-dried culture of *Staphylococcus hyicus* was prepared for testing by inoculating it into a nutrient broth and incubating at 37° C. for 18 hours on a shaking waterbath. At testing, the culture had a density of 1 to $2 \times 10^9$ cells per milliliter.

A 1% by weight stock suspension of magnesium sulfate trihydrate adduct of 2,2'-dithiobis-pyridine-1,1'-dioxide was made and autoclaved at 121° C. for 20 minutes.

To 2.0 milliliters of top agar containing 0.75% by weight agar in Vogel-Bonner minimal media[1] to yield concentrations of 0, 0.1, 1.0, 10, 100, and 1000 parts of that compound per million parts of solution. After vortexing, the contents of the tubes were prepared into nutrient agar plates and incubated for 18 hours at 37° C. Five plates were prepared at each dose level of magnesium sulfate trihydrate adduct of 2,2'-dithiobis-pyridine-1,1'-dioxide.

[1]Vogel, H. J. and D. M. Bonner (1956) Acetylornithinase of *Escherichia coli:* partial purification and some properties, *J. Biol. Chem.*, 218:97–106.

The colonies of each plate were counted on an NBS Biotran II automatic colony counter. The average value of lethality observed of the 5 plates of each does are given in Table 1 below.

TABLE 1

| Test Material | Percent Kill at Concentration of Test Material (ppm in top agar) | | | | | |
|---|---|---|---|---|---|---|
| | 0 | 1000 | 100 | 10 | 1 | 0.1 |
| Magnesium sulfate trihydrate adduct of 2,2'-dithiobis-pyridine-1,1'-dioxide | 0% | 100% | 100% | 100% | 96% | 0% |

The MLC is generally defined as that concentration of test material lethal to 99% or more by weight of the organisms plated. As can be seen in Table 1, the MLC for magnesium sulfate trihydrate adduct of 2,2'-dithiobis-pyridine-1,1'-dioxide was 10 ppm.

EXAMPLE 2

A clinical study was carried out to assess the effectiveness of magnesium sulfate trihydrate adduct of 2,2'-dithiobis-pyridine-1,1'-dioxide in the treatment of swine exudative epidermitis. Ten young pigs with clinical signs of exudative epidermitis were sprayed with about 20 to about 30 ml of an aqueous suspension containing 1.5% by weight magnesium sulfate trihydrate adduct of 2,2'-dithiobis-pyridine-1,1'-dioxide daily for 5 days. Separately, a control group of 9 young pigs with similar clinical signs were sprayed with same aqueous vehicle daily, except no magnesium sulfate trihydrate adduct of 2,2'-dithiobis-pyridine-1,1'-dioxide was in this vehicle.

The severity of the disease was scored for each pig for 5 days during treatment and then at 3 and 13 days post treatment using the following 1 to 5 scoring system:

1. Normal

2. Very mild exudative epidermitis (EE) (about 15% of body surface affected)
3. Moderate EE (about 15% to about 20% of body surface affected).
4. Moderate EE to Severe EE (about 25% to about 50% of the body affected)
5. Very severe EE (more than about 50% of body affected)

Death was given no point value in this system.

The results of the scoring of this study are given in Tables 2 and 3.

An indicator of effectiveness of treatment is clinical improvement. For the purposes of this study, clinical improvement was defined as a reduction of the day 1 score by one or more units by day 18. Approximately 70% of the test animals exhibited clinical improvement as compared with only 11% of the controls.

Therefore, it could be reasonably concluded that the repeated dermal application of 1.5% suspension magnesium sulfate trihydrate adduct of 2,2'-dithiobis-pyridine-1,1'-dioxide to pigs with clinical signs of swine exudative epidermitis resulted in significant improvement of the clinical signs compared to similarly treated vehicle control animals.

TABLE 2

Individual Scores[a] of Young Pigs Receiving 1.5% Magnesium Sulfate Trihydrate Adduct of 2,2'-Dithiobis-Pyridine-1,1'-Dioxide Dermally Over the 18-Day Observation Period

| Pig No. | Day 1 | 2 | 3 | 4 | 5 | 8 | 18 |
|---|---|---|---|---|---|---|---|
| 1 | 2 | 2 | 2 | 1 | 2 | 1 | 1 |
| 2 | 3 | 3 | 3 | 3 | 3 | 3 | 2 |
| 3 | 1 | 1 | 1 | 1 | 1 | 1 | 1 |
| 4 | 4 | 4 | 4 | 4 | 4 | 3 | 1 |
| 5 | 1 | 1 | 1 | 2 | 2 | 2 | 1 |
| 6 | 1 | 2 | 2 | 2 | 1 | 1 | 1 |
| 7 | 1 | 1 | 1 | 1 | 1 | 1 | 0 |
| 8 | 1 | 1 | 1 | 1 | 1 | 1 | 0 |
| 9 | 1 | 1 | 1 | 1 | 1 | 1 | 0 |
| 10 | 1 | 1 | 1 | 1 | 1 | 2 | 1 |

[a] 1 = normal; 2 = very mild EE; 3 = moderate EE; 4 = moderate to severe EE; 5 = very severe EE

TABLE 3

Individual Scores[a] of Control Young Pigs Receiving Only Vehicle Dermally Over the 18 Day Observation Period

| Pig No. | Day 1 | 2 | 3 | 4 | 5 | 8 | 18 |
|---|---|---|---|---|---|---|---|
| C1 | 1 | 1 | 2 | 2 | 2 | 2 | Dead |
| C2 | 2 | 2 | 2 | 2 | 2 | 2 | 1 |
| C3 | 1 | 1 | 1 | 1 | 1 | 1 | 1 |
| C4 | 1 | 1 | 1 | 1 | 1 | 1 | 1 |
| C5 | 1 | 1 | 1 | 1 | 1 | 1 | 1 |
| C6 | 3 | 3 | 3 | 3 | 3 | 3 | 3 |
| C7 | 1 | 1 | 1 | 1 | 1 | 1 | 1 |
| C8 | 2 | 2 | 2 | 2 | 1 | 1 | 2 |
| C9 | 2 | 2 | 2 | 2 | 2 | 1 | 1 |

[a] 1 = normal; 2 = very mild EE; 3 = moderate EE; 4 = moderate to severe EE; 5 = very severe EE

What is claimed is:

1. A method of treating an animal for swine exudative epidermitis which comprises administering to said animal an effective amount of at least one pyridine-N-oxide disulfide compound to treat or prevent swine exudative epidermitis; said pyridine-N-oxide disulfide compound selected from (a) 2,2'-dithiobis-pyridine-1,1'-dioxide and (b) adducts of 2,2'-dithiobis-pyridine-1,1'-dioxide, the adducts having the formula $$(C_5H_4NOS)_2MY_t$$

wherein M is an alkaline earth metal selected from the group consisting of calcium, magnesium, barium and strontium, Y is an anion selected from the group consisting of halides, sulfates, nitrates, chlorates and acetates, and t is either 1 or 2.

2. The method of claim 1 wherein said administration is applied to the skin of a pig.

3. The method of claim 2 wherein from 1 to about 5 doses of an aqueous suspension containing about 15 to about 200 milliliters of water containing from 1.0% to 5.0% by weight of magnesium sulfate trihydrate adduct of 2,2'-dithiobis-pyridine-1,1'-dioxide are administered to the skin of said pig at intervals of 12 to 48 hours.

4. The method of claim 2 wherein said pig is treated when it has the clinical symptoms of the disease.

5. The method of claim 2 wherein said pig is under about 3 months in age.

* * * * *

UNITED STATES PATENT AND TRADEMARK OFFICE
CERTIFICATE OF CORRECTION

PATENT NO. : 4,609,665

DATED : September 2, 1986

INVENTOR(S) : Davidson et al

It is certified that error appears in the above-identified patent and that said Letters Patent is hereby corrected as shown below:

In column 2, at line 34 after "to" and before "in" insert --treat or prevent swine exudative epidermitis as used--.

Signed and Sealed this

Eleventh Day of November, 1986

Attest:

DONALD J. QUIGG

Attesting Officer      Commissioner of Patents and Trademarks